United States Patent [19]

Amalric et al.

[11] Patent Number: 5,670,471

[45] Date of Patent: Sep. 23, 1997

[54] CONCENTRATE COMPRISING ALKYLGLYCOSIDE MIXTURE AND FATTY ALCOHOL AND CORRESPONDING METHODS OF USE

[75] Inventors: Chantal Amalric, Blan; Nelly Lecocu-Michel, Maisons-Alfort, both of France

[73] Assignee: Societe d'Exploitation de Produits pour les Industries Chimiques, S.E.P.P.I.C., Paris, France

[21] Appl. No.: 549,675

[22] PCT Filed: Nov. 16, 1994

[86] PCT No.: PCT/FR94/01336

§ 371 Date: Nov. 8, 1995

§ 102(e) Date: Nov. 8, 1995

[87] PCT Pub. No.: WO95/13863

PCT Pub. Date: May 26, 1995

[30] Foreign Application Priority Data

Nov. 19, 1993 [FR] France ............... 93 13895

[51] Int. Cl.$^6$ ................ C11D 3/22; C11D 3/20; A61K 7/00; B01F 17/56

[52] U.S. Cl. ................ 510/416; 424/70.31; 510/119; 510/135; 510/136; 510/137; 510/151; 510/152; 510/155; 510/158; 510/159; 510/417; 510/470; 510/505; 510/535; 514/846

[58] Field of Search ............... 510/470, 505, 510/535, 119, 130, 135–138, 158, 159, 405, 416, 417, 421, 422, 151, 152, 155; 514/846; 424/70.31

[56] References Cited

U.S. PATENT DOCUMENTS

| | | | |
|---|---|---|---|
| 5,370,816 | 12/1994 | Balzer et al. | 510/340 |
| 5,494,938 | 2/1996 | Kawa et al. | 514/786 |
| 5,529,721 | 6/1996 | Salka et al. | 510/123 |

FOREIGN PATENT DOCUMENTS

| | | |
|---|---|---|
| 0 070 074 | 1/1983 | European Pat. Off. . |
| 474915 | 3/1992 | European Pat. Off. . |
| 2 702 482 | 9/1994 | France . |
| 2 702 769 | 9/1994 | France . |
| 92 06778 | 4/1992 | WIPO . |

OTHER PUBLICATIONS

Rohm and Haas, "Triton CG–110" Brochure, *International Division Technical Bulletin Life Science Section*, May 1975.

*Primary Examiner*—Ardith Hertzog
*Attorney, Agent, or Firm*—Oliff & Berridge

[57] ABSTRACT

A concentrate that is particularly useful as a pearling agent or for preparing emulsions is provided. The concentrate includes from 60 to 90% by weight of a mixture of at least one alkylglycoside of the formula $RO(G)_x$ and of at least one alkylglycoside of the formula $R'O(G')_{x'}$. R represents a saturated or unsaturated linear or branched aliphatic radical containing from 8 to 15 carbon atoms. R' represents a saturated or unsaturated linear or branched aliphatic radical containing from 16 to 22 carbon atoms. G and G', which are identical or different, represent a saccharide residue. The subscripts x and x', which are identical or different, represent a number between 1 and 10. The concentrate also includes from 10 to 40% by weight of at least one fatty alcohol of the formula $R_1OH$, $R_1$ being a saturated or unsaturated linear or branched aliphatic radical containing from 8 to 22 carbon atoms.

31 Claims, No Drawings

CONCENTRATE COMPRISING ALKYLGLYCOSIDE MIXTURE AND FATTY ALCOHOL AND CORRESPONDING METHODS OF USE

FIELD OF THE INVENTION

The present invention relates to a concentrate comprising a mixture of alkylglycosides and at least one fatty alcohol, as well as to uses of these concentrates, in particular as pearling agent or for preparing emulsions.

BACKGROUND OF THE INVENTION

Alkylglycosides are well-known compounds.

They may be prepared in particular according to the processes described in French Patent Application 93.02877 filed on Mar. 12, 1993 and French Patent Application 93.03188 filed on Mar. 19, 1993, both in the name of the Applicant.

They may be used as surfactants, alone or in combination with other surfactants, in numerous applications. In this regard, reference may be made, for example, to the brochure Triton CG 110 of May 1975, distributed by the company Rohm & Haas or to patent application EP-A-70,074, which describe compositions and formulations combining surfactants and alkylglycosides, these being useful in particular in detergency or in cosmetics.

The application for patent WO 92/06778, in the name of the Applicant, describes compositions comprising 60 to 90% by weight of at least one fatty alcohol having from 12 to 22 carbon atoms and from 10 to 40% by weight of an alkylpolyoside (or alkylglycoside), the alkyl part of which may be identical to that of the fatty alcohol.

These compositions are useful as self-emulsifiable agents.

SUMMARY OF THE INVENTION

A first subject of the present invention consists of a composition in the form of an alkylglycoside-based concentrate having properties which, as far as the Applicant is aware, have never been obtained or achieved beforehand using alkylglycosides.

A second subject of the present invention consists of the use of the said concentrate as a pearling agent, for the purpose of producing a pearlescent appearance which is stable over time.

A third subject of the present invention consists of the use of the said concentrate for the preparation of emulsion, in particular of fluid emulsions such as milks, which are stable over time.

A fourth subject of in the invention consists of compositions, in particular cleansing soaps or syndets, containing the concentrate, which is of little or no irritance to man or animals.

A fifth subject of the invention consists of foaming compositions comprising an emulsified oil phase, which is stable over time.

DETAILED DESCRIPTION OF PREFERRED EMBODIMENT

According to a first aspect of the invention, it consists of a concentrate comprising:

i) from 60 to 90% by weight of a mixture of at least one alkylglycoside of formula (I) and of at least one alkylglycoside of formula (II):

$$RO(G)_x \quad (I)$$
$$R'O(G')_{x'} \quad (II)$$

in which:

R represents a saturated or unsaturated linear or branched aliphatic radical containing from 8 to 15 carbon atoms.

R' represents a saturated or unsaturated linear or branched aliphatic radical containing from 16 to 22 carbon atoms.

G and G', which are identical or different, represent a saccharide residue.

x and x', which are identical or different, represent a number between 1 and 10, ii) from 10 to 40% by weight of at least one fatty alcohol of formula $R_1OH$, $R_1$ being a saturated or unsaturated linear or branched aliphatic radical containing from 8 to 22 carbon atoms.

The concentrate according to the invention may be used in particular as a pearling agent in order to provide a pearling effect which is homogeneous and stable over time. This is entirely surprising insofar as compositions such as those described in the application for patent WO 92/06778 mentioned above cannot impart such a pearling effect.

The alkylglycosides of formulae (I) and (II) may contain, as saccharide residue G or G', a glucose, mannose, galactose, idose, arabinose, xylose, ribose, gulose, lyxose or fructose residue. Advantageously, G and G' are identical and each represent a glucose residue. G and G' may be in α or β anomeric form, and the saccharide unit may be in furanoside or pyranoside form.

The indices x and x' represent the average degree of polymerization of the saccharide residue. They preferably represent a number between 1.05 and 2.5, more preferably between 1.05 and 1.35.

It is noted that, when at least one of x and x' is equal to 1, the corresponding alkylglycoside may be classified as an alkylmonoglycoside. When one of x or of x' is greater than 1, the corresponding alkylglycoside may be classified as an alkylpolyglycoside.

Within the concentrate according to the invention, the weight ratio between the said alkylglycosides of formula (I) and those of formula (II) is usually between 3/1 and 1/3; it is preferably between 2/1 and 1/2.

The alkylglycosides of formula (I) have a radical R which may preferably contain from 10 to less than 16 carbon atoms, preferably from 12 to less than 16 carbon atoms.

The alkylglycosides of formula (II) which constitute the concentrate are most particularly those for which R' is a radical containing 16 and/or 18 carbon atoms.

The radicals R, R' and $R_1$ are advantageously saturated aliphatic radicals, that is to say alkyl radicals.

The concentrate according to the invention usually comprises a mixture of at least two fatty alcohols. The radical $R_1$ of each of these fatty alcohols is preferably identical to each of the radicals R and R'. The said fatty alcohol mixture then consists, on the one hand, of at least one fatty alcohol containing from 8 to less than 16 carbon atoms, preferably from 10 to less than 16 carbon atoms, more preferably from 12 to less than 16 carbon atoms, and, on the other hand, of at least one fatty alcohol containing from 16 to 22 carbon atoms, preferably from 16 to 18 carbon atoms. This mixture of fatty alcohols more particularly contains at least 80% by weight, preferably from 90 to 99% by weight, of one or more fatty alcohols containing 16 or more carbon atoms.

A concentrate according to the invention usually comprises from 15 to 38%, preferably from 25 to 38%, by weight of at least one fatty alcohol.

Besides the alkylglycosides and fatty alcohols mentioned above, the said concentrate may contain a saccharide and/or polysaccharide at a concentration of less than or equal to 5% by weight.

The concentrates according to the invention may be prepared simply by mixing together their constituents in proportions as mentioned above.

However, on the industrial scale, they are preferably prepared according to one of the two routes used conventionally for the synthesis of alkylglycosides.

The first route comprises the reaction, in acidic medium, between a fatty alcohol and a saccharide bearing an anomeric OH, such as glucose or dextrose.

The second route consists:

in a first step, in preparing a first alkylpolyglycoside by performing an etherification reaction between a light alcohol such as, for example, methanol or butanol, and a saccharide such as glucose, in order to obtain compounds such as methylglucoside or butylglucoside; then, in a second step, in carrying out a transetherification with a heavy fatty alcohol such as those mentioned above, with distillation of the light alcohol.

Each of these two routes may be, if appropriate, completed by operations of neutralization, of filtration, of decolorization and of removal of the excess fatty alcohol. This removal may take place by distillation, in particular using a thin-film evaporator, so as to make it possible to obtain a fatty alcohol concentration as specified above.

Usually, the concentrates thus prepared are solid at room temperature. They may be in the form of flakes.

According to another aspect of the invention, it relates to the use of the concentrates described above in various applications. Thus, the said concentrates may form part of the formation of various compositions, which are described below.

One of the main uses of the concentrates of the invention is, as mentioned above, that of pearling agent. The pearlescent appearance produced by the said concentrates is usually obtained by various types of solid, organic or inorganic crystals, such as fatty acid esters, mica or bismuth oxychloride. Without being bound by theory, it appears that the concentrate according to the invention affords a pearlescent appearance by formation of liquid crystals or droplets which reflect light. The term "pearling agent" is also understood here to refer to an agent which produces an iridescent, moiré, metallic or opacifying appearance or effect.

It is particularly notable that the pearlescent appearance produced by a concentrate according to the invention is homogeneous and stable over time.

The compositions which may contain, as pearling agent, the concentrate according to the invention may be chosen from the following foaming compositions: pharmaceutical, cosmetic or hygiene compositions, such as shampoos, liquid soaps, shower gels, bubble baths, make-up-removing gels for the face or detergent compositions, in particular washing-up detergents and liquid washing products. In this type of composition, the concentrate according to the invention may act as a foaming surfactant.

The concentration of concentrate according to the invention in such a composition may be between 2 and 15% by weight.

The compositions mentioned may also contain surfactants, in particular foaming surfactants. Surfactants which may be mentioned are:

amphoteric surfactants, in particular betaine and derivatives thereof such as alkylbetaines, for instance N-alkylbetaines or C-alkylbetaines, N-alkylaminobetaines, alkylamidobetaines, alkylphosphoamidobetaines or alkylphosphobetaines, sultaine and derivatives thereof, such as alkylamidosulfobetaines, imidazoline derivatives, N-alkylglycines, N-alkyl-β-alanines, alkylpolyaminecarboxylates and N-alkylaminobutyrates.

Preferred amphoteric surfactants are chosen from cocoamidobetaine, cocobetaine, cocoamidosultaine, cocoamidopropylbetaine, stearylbetaine, stearylamphocarboxylic glycinate, cocoamidopropylhydroxysulfobetaine, cocoamphocarboxyglycinate, cocoimidazoline carboxylate or the cocoamidopropyl dimethylaminohydroxypropyl hydrolysate of collagen (according to the CFTA-Cosmetic Toiletries Fragrance Association).

nonionic surfactants, in particular copra amides, polysorbates, hydrogenated and polyoxyethylenated (EO) and/or polyoxypropylenated (PO) castor oils, EO and/or PO alkylphenols, or alkylglycosides such as those of formulae (I) and (II) mentioned above.

cationic surfactants, in particular those of the quaternary ammonium type or amine oxides.

and, advantageously, anionic surfactants, in particular those mentioned in patent application EP-A-70,074, such as carboxylates, sulfonates and, especially, sulfates. Among the latter, alkyl sulfates and alkyl ether sulfates neutralized with a cation, such as sodium, potassium, magnesium or ammonium cations, are preferred. Sodium lauryl ether sulfates are surfactants most particularly preferred.

Moreover, the said foaming compositions may contain an emulsified oil phase. Generally, these compositions contain the said oil phase and at least one of the surfactants mentioned above. Such compositions may consist of shampoos, washing-up liquids and, most particularly, 2-in-1 shower gels, that is to say shower gels simultaneously having a cleansing power and a hydrating power.

Conventional compositions, containing an oil phase and at least one foaming surfactant, are usually unstable over time, that is to say that the said oil phase separates out.

In order to overcome this instability, a stabilizing agent such as thickening polymers is incorporated therein. However, it could be seen, surprisingly, that the presence in these compositions of the concentrate according to the invention makes it possible to impart great stability over time to the oil phase, even in the absence of these stabilizing agents.

The compositions generally contain, by weight, from 2 to 15% of the said concentrate, from 2 to 50%, preferably from 5 to 30%, of at least one surfactant, from 0.5 to 15% of oil and an aqueous phase.

The oil may be of mineral, plant, animal or synthetic origin. Silicone oils such as dimethicone, Monoi oil, sweet almond oil, liquid paraffin and synthetic triglycerides may be mentioned in particular.

According to another aspect, the invention relates to the use of the said concentrate for the preparation of emulsions, these emulsions being of the water-in-oil, oil-in-water or oil-in-water-in-oil type.

The said concentrate is most particularly suitable for the preparation of fluid emulsions which are stable over time.

It is noted that it is entirely surprising that such fluid emulsions, which may remain stable for more than 3 months, can be prepared with a concentrate according to the invention, insofar as neither alkylglycosides nor alcohols allow them to be otherwise obtained.

Within the context of the invention, the term "fluid emulsion" is understood to refer to an emulsion whose flow through a 6 mm ISO 2431 flow cup starts less than 5 seconds after removal of the stopper (test according to international standard ISO 2431).

Fluid emulsions which may be mentioned in particular are milks, in particular milks of the oil-in-water type, for cosmetic or hygiene use, such as makeup-removing milks, body milks or sun milks.

The said emulsions may contain from 1 to 15% by weight of the said concentrate. The oil phase of these emulsions may consist of one or more oils as mentioned above.

The compositions and emulsions described above may be prepared in a manner known by those skilled in the art, for example simply by mixing together their constituents. The concentrate according to the invention may be used as it is or in the melted state.

It is generally possible to use it in the form of a pearling base consisting of a dispersion of the said concentrate in a suitable liquid. Such a liquid is usually water, but it may also comprise an organic solvent.

The concentration of the said concentrate in a pearling base may be between 1 and 50% by weight, preferably between 2 and 25% by weight.

Such a pearling base constitutes another aspect of the invention, as does its use as a pearling agent and for preparing emulsions.

According to another aspect, the invention is also intended to encompass syndets, or dermatological cleansing bars, comprising a concentrate according to the invention, as well as one or more foaming surfactants such as those mentioned above, with the exclusion of soaps.

These syndets usually also contain at least one conventional plasticizer, binder or texturizing agent, such as polyethylene glycols (PEG), maltodextrins or fatty alcohols.

A syndet according to the invention generally comprises from 2 to 40% by weight, preferably from 10 to 35% by weight, of the said concentrate, from 20 to 50% by weight of at least one foaming surfactant and from 10 to 40% by weight of at least one plasticizer, binder or texturizing agent.

The syndets according to the invention, containing the said concentrate, have improved plasticity, a better foam feel and increased skin tolerance. They may be prepared in a manner known to those skilled in the art, from the concentrate in the melted state.

According to another aspect, the invention also relates to cleansing soaps comprising the said concentrate defined above, at least one surfactant soap and, where appropriate, at least one softener, such as glycerol.

The said surfactant, soap may consist of a fatty acid, in particular a fatty acid of animal or plant origin, such as tallow or copra fatty acid, neutralized with sodium hydroxide.

A cleansing soap according to the invention usually comprises from 1 to 20% by weight of the said concentrate, from 65 to 95% by weight of at least one soap and, where appropriate, from 3 to 15% by weight of at least one softener. It may be prepared in a manner known to those skilled in the art from the concentrate in the melted state.

The compositions, emulsions, syndets and cleansing soaps mentioned above may also comprise other conventional additives such as dyes, fragrances, preservatives or viscosity modifiers or thickeners.

The examples which follow are intended to illustrate the present invention.

Except where otherwise mentioned, in these examples, all the % are given by weight.

The compounds below are mentioned in some of the examples. Their definitions are as follows:

Acrysol 22: acrylate/steareth-20 methacrylate copolymer (Rohm & Haas Company),
Sepigel 305: acrylic copolymer (SEPPIC company)
Oramix NS10: decylpolyglucoside (SEPPIC company)
NaLES: sodium lauryl ether sulfate
Carbomer 941: acrylic polymer (GOODRICH Company)

EXAMPLE 1

Preparation of an alkylglycoside-containing concentrate 6.30 kg of anhydrous glucose and 51.5 kg of fatty alcohol consisting (% by weight) of 20% of dodecanol, 28% of tetradecanol, 17% of hexadecanol and 35% of octadecanol are reacted together in a multi-purpose reactor under vacuum, at a temperature of about 100° C. and in the presence of a catalytic system consisting of 57 g of sulfuric acid and 41 g of 50% hypophosphorous acid.

After 5 hours, the reaction is completed and the reaction mixture is neutralized with 0.1 kg of sodium hydroxide, filtered and the excess fatty alcohol is partially removed by distillation on a thin-film evaporator to give 14 kg of a concentrate comprising (% by weight).

| Dodecanol | 0.3% |
| --- | --- |
| Tetradecanol | 1.6% |
| Hexadecanol | 4.5% |
| Octadecanol | 27.9% |
| Dodecylpolyglucoside | 14.4% |
| Tetradecylpolyglucoside | 18.9% |
| Hexadecylpolyglucoside | 10.9% |
| Octadecylpolyglucoside | 21.5% |

The characteristics of this concentrate are as follows:

| Acid number | 0.4 |
| --- | --- |
| Hydroxyl number | 445 |
| pH (1%) | 5.05 |
| Color (Gardner) | 2 |
| Melting point | 57° C. |

EXAMPLE 2

Preparation of an alkylglycoside-containing concentrate

Under the conditions of Example 1, 6.45 kg of glucose and 50 kg of fatty alcohols consisting (% by weight) of 10% of decanol, 9% of dodecanol, 21% of tetradecanol, 32% of hexadecanol and 28% of octadecanol are reacted together.

The concentrate obtained comprises (% by weight)

| Decanol | 0.1% |
| --- | --- |
| Dodecanol | 0.1% |
| Tetradecanol | 1.4% |
| Hexadecanol | 8.9% |
| Octadecanol | 19.9% |
| Decylpolyglucoside | 8.2% |
| Dodecylpolyglucoside | 6.8% |
| Tetradecylpolyglucoside | 14.9% |
| Hexadecylpolyglucoside | 21.6% |
| Octadecylpolyglucoside | 18.1% |

The characteristics of this concentrate are as follows:

| Acid number | 0.3 |
| --- | --- |
| Hydroxyl number | 469 |
| pH (1%) | 5.4 |
| Color (Gardner) | 2 |
| Melting point | 58° C. |

EXAMPLE 3

Preparation of an alkylglycoside-containing concentrate

Under the conditions of Example 1, 6.5 kg of glucose and 50 kg of fatty alcohols consisting (% by weight) of 17% of dodecanol, 22% of tetradecanol, 39% of hexadecanol and 22% of octadecanol are reacted together.

The concentrate obtained comprises (% by weight)

| | |
|---|---|
| Dodecanol | 0.3% |
| Tetradecanol | 1.4% |
| Hexadecanol | 13.9% |
| Octadecanol | 20.2% |
| Dodecylpolyglucoside | 11.9% |
| Tetradecylpolyglucoside | 14.5% |
| Hexadecylpolyglucoside | 24.3% |
| Octadecylpolyglucoside | 13.1% |

The characteristics of this concentrate are as follows:

| | |
|---|---|
| Acid number | 0.3 |
| Hydroxyl number | 462 |
| pH (1%) | 5.3 |
| Color (Gardner) | 3 |
| Melting point | 57° C. |

EXAMPLE 4

Various dispersions in water of mixtures of alkylpolyglucosides (APG) and of fatty alcohols were prepared. Each of these dispersions had a solids content of 15%.

Dispersion 1, according to the invention, was prepared from the concentrate of Example 2.

Dispersion 2, for comparison, had a solids content of the following composition:

| | |
|---|---|
| Decylpolyglucoside | 28.2% |
| Dodecylpolyglucoside | 2.4% |
| Tetradecylpolyglucoside | 2.4% |
| Cetyl alcohol | 33.5% |
| Stearyl alcohol | 33.5% |

Dispersion 3, for comparison, had a solids content of the following composition:

| | |
|---|---|
| Hexadecylpolyglucoside | 25% |
| Octadecylpolyglucoside | 25% |
| Hexadecanol | 25% |
| Octadecanol | 25% |

The solids contents (in %) of each of the dispersions 1 to 3, expressed as APG and fatty alcohols having, on the one hand, an alkyl part containing less than 16 carbon atoms and, on the other hand, an alkyl part containing more than 16 carbon atoms, are summarized in Table I below.

TABLE I

| Dispersion | APG < C16 | APG ≧ C16 | Alcohol < C16 | Alcohol ≧ C16 |
|---|---|---|---|---|
| 1 | 29.9 | 39.7 | 1.6 | 28.8 |
| 2 | 33 | 0 | 0 | 67 |
| 3 | 0 | 50 | 0 | 50 |

From each of the dispersions 1 to 3, foaming compositions 1, 2 and 3 were prepared, comprising:

| | |
|---|---|
| Dispersion 1, 2 or 3 | 20% |
| Na LES | 12.5% |
| Acrysol 22 | 3% |
| Water qs | 100% |

The appearance and the stability of each of the dispersions 1 to 3 and of the compositions 1 to 3 were then examined.

The results obtained are featured in Table II.

TABLE II

| Product tested | Appearance | Stability |
|---|---|---|
| Dispersion 1 | Pearlescent, fluid and Hom. | 1 month |
| Dispersion 2 | Non-pearlescent and Het. | 1 day |
| Dispersion 3 | Pasty, non-pearlescent | 7 days |
| Composition 1 | Pearlescent and Hom. | more than 3 months |
| Composition 2 | Non-pearlescent | 1 day |
| Composition 3 | Non-pearlescent and Het. | at least 7 days |

Het.: Heterogeneous appearance
Hom.: Homogeneous appearance

The results of Table II show that a dispersion or a composition containing a concentrate according to the invention has a pearlescent appearance which is homogeneous and stable over time.

EXAMPLE 5

In order to evaluate the stability of a composition comprising an emulsified oil phase, a composition, according to the invention, of the 2-in-1 shower gel type was prepared, comprising:

| | |
|---|---|
| Concentrate of Example 3 | 5% |
| Na LES | 12.5% |
| Oil | 1 or 5% |
| Acrysol 22 | 3% |
| Water | qs 100% |
| Sodium hydroxide | qs pH = 7.2 |

By way of comparison, a control composition not containing the concentrate of Example 3 was prepared.

The stability of each of these compositions was tested at 40° C.

The results obtained are featured in Table III below.

TABLE II [sic]

| Oil | Control composition | Composition according to the invention |
|---|---|---|
| Dimethicone 1% | — | Stable for at least 15 days |
| Dimethicone 5% | Unstable | Stable for at least 25 days |
| Copra caprylate/caprate (50/50 mixture) 1% | — | Stable for at least 15 days |
| Copra caprylate/caprate (50/50 mixture) 5% | Unstable | Stable for at least 15 days |

EXAMPLE 6

The stability at 40% was tested of various oil-in-water emulsions containing or not containing variable concentrations of a usual stabilizing agent: Carbomer 941

The emulsions all contained 3% of the concentrate of Example 1.

The nature and concentration of the oils, the concentration of Carbomer 941, and the stability results obtained are featured in Table IV below.

TABLE IV

| Emulsion | Carbomer 941 | | | |
|---|---|---|---|---|
| | 0% | 0.01% | 0.05% | 0.1% |
| 1: 5% liquid paraffin | >7 | — | >7 | >7 |
| 2: 10% liquid paraffin | >7 | >7 | >7 | — |
| 3: 5% glycerol tri-heptanoate | >7 | — | >7 | >7 |
| 4: 10% glycerol tri- | >7 | — | >7 | >7 |

The symbol ">7" means that the emulsion remained stable for at least 7 days.

It can be seen that all the emulsions tested, whether or not they contain the stabilizing agent, are stable for at least 7 days. These results show that an emulsion containing a concentrate according to the invention does not require the additional presence of a conventional stabilizer.

Examples 7 to 13 relate to cosmetic or hygiene compositions which may be prepared using a concentrate according to the invention. In each of these examples, the term "APG" is used to denote the concentrate of Example 2.

EXAMPLE 7

LIQUID SOAP

FORMULA

| A | APG | 4.00% |
|---|---|---|
| | WATER | 30.00% |
| B | NaLES | 5.00% of active ingredient |
| | ORAMIX NS10 | 5.00% of active ingredient |
| | WATER | qs 100% |
| C | ACRYSOL 22 | 2.00 to 3.00% |
| | WATER | 10.00% |
| D | FRAGRANCE | qs |
| | PRESERVATIVE | qs |
| | SODIUM HYDROXIDE | qs pH = 7 |

PROCEDURE

Melt the APG in the water at about 60° C. (phase A). Allow to cool to 30° C. then incorporate phase B, followed by phase C and then phase D. Lastly, adjust the pH.

CHARACTERISTICS

Opaque emulsion-type appearance Viscosity 3000 mPa.s (Brookfield LVT4 6 rpm)

EXAMPLE 8

ALMOND OIL SHAMPOO

FORMULA

| A | APG | 4.00% |
|---|---|---|
| | SWEET ALMOND OIL | 1.00% |
| | WATER | 30.00% |
| B | NaLES | 8.00% of active ingredient |
| | ORAMIX NS 10 | 2.00% of active ingredient |
| | AMONYL 675 SB [1] | 2.00% of active ingredient |
| | WATER | qs 100% |
| C | ACRYSOL 22 | 2.00 to 3.00% |
| | WATER | 10.00% |
| D | FRAGRANCE | qs |
| | PRESERVATIVE | qs |
| | SODIUM HYDROXIDE | qs pH = approximately 7 |

[1] Cocoamidopropylhydroxysultaine marketed by the SEPPIC Company.

PROCEDURE

Melt the APG in the water at about 60° C., and incorporate the sweet almond oil (phase A). Allow to cool to 30° C., then incorporate phase B, followed by phase C and then phase D. Lastly, adjust the pH.

CHARACTERISTICS

Pearlescent emulsion-type appearance, stable for at least 3 months (despite the absence of stabilizer).
Viscosity 300 mPa.s (Brookfield LVT4 6 rpm).

EXAMPLE 9

MAKEUP-REMOVING MILK

FORMULA

| A | APG | 3.00% |
|---|---|---|
| | THICK LIQUID PARAFFIN | 10.00% |
| B | WATER | qs 100% |
| | CARBOMER 941 | 0.05% |
| C | FRAGRANCE | qs |
| | PRESERVATIVE | qs |
| | SODIUM HYDROXIDE | qs pH = 7 approximately |

PROCEDURE

Melt A at about 75° C. Disperse Carbomer 941 in the aqueous phase with high shear and heat to about 75° C. Emulsify phase B in phase A then, at about 30° C., add phase C and the amount of base required to adjust the pH.

CHARACTERISTICS

Fluid emulsion having a rich texture
Flow time of less than 5 seconds (ISO Standard 2431—6 mm flow cup)
Stability of more than 3 months at room temperature.

EXAMPLE 10

BODY MILK

FORMULA

| A | APG | 3.00% |
|---|---|---|
| | GLYCEROL TRIHEPTANOATE | 10.00% |
| B | WATER | qs 100% |
| C | SEPIGEL 305 | 1.00% |
| D | FRAGRANCE | qs |
| | PRESERVATIVE | qs |

PROCEDURE

Melt A at about 75° C. Heat the water to about 75° C. Emulsify B in A. Add C at about 60° C. then, at about 30° C. add D.

CHARACTERISTICS

Fluid emulsion having a rich texture
Stable for at least three months at room temperature
Flow time of less than 5 seconds (ISO Standard 2431—6 mm flow cup).

EXAMPLE 11

| SUN MILK | | |
|---|---|---|
| FORMULA | | |
| A | APG | 3.00% |
|   | SESAME OIL | 5.00% |
|   | PARSOL MCX [1] | 5.000% |
|   | λCARRAGEENAN | 0.10% |
| B | WATER | qs 100% |
| C | SEPIGEL 305 | 0.80% |
| D | FRAGRANCE | qs |
|   | PRESERVATIVE | qs |

[1] Octyl para-methoxycinnamate marketed by the company GIVAUDAN.

PROCEDURE

Melt the APG in the oil at about 75° C. Add the carrageenan and the Parsol. Heat the water to about 75° C. Emulsify B in A. Add C at about 60° C. then, at about 30° C., add D and adjust the PH [sic] if necessary.

CHARACTERISTICS:

Fluid emulsion having a rich texture.
Stable for at least 3 months at room temperature.
Flow time of less than 5 seconds (ISO Standard 2431—6 mm flow cup)

EXAMPLE 12

| SHAMPOO | | |
|---|---|---|
| FORMULA | | |
| A | APG | 4.00% |
|   | ELFACOS GT282S [1] | 2.00% |
|   | DIMETHICONE 50 mPa · s | 1.00% |
|   | WATER | 30.00% |
| B | NaLES | 8.00% |
|   | AMONYL 380BA [2] | 5.00% |
|   | WATER | qs 100% |
| C | JAGUAR C13S [3] | 0.50% |
|   | WATER | 10.00% |
| D | FRAGRANCE | qs |
|   | PRESERVATIVE | qs |

[1] Hydrogenated talloweth - 60 myristyl glycol, marketed by the company AKZO
[2] Cocoamidopropylbetaine, marketed by the company SEPPIC
[3] Hydroxylpropylguar, marketed by the company RHONE POULENC

PROCEDURE:

Melt the APG and the ELFACOS together in the water at about 60° C. and add the DIMETHICONE (phase A). Allow to cool to 30° C. then incorporate phase B, followed by phase C and then phase D. Lastly, adjust the PH [sic] to about 5.0.

CHARACTERISTICS:

Opaque emulsion-type appearance Viscosity 1000 mPa.s (Brookfield LVT4 6 rpm)

EXAMPLE 13

| 2-in-1 SHOWER GEL (cleansing and hydrating) | | |
|---|---|---|
| FORMULA | | |
| A | APG | 3.50% |
|   | 50/50 COPRA | 4.00% |
|   | CAPRYLATE/CAPRATE | 4.00% |
|   | MONOI OIL | 1.00% |
|   | WATER | 30.00% |
| B | NaLES | 12.00% of active ingredient |
|   | ELFAN OS46A [1] | 4.00% of active ingredient |
|   | WATER | qs 100% |
| C | ACRYSOL 22 | 2 to 3.00% |
|   | WATER | 10.00% |
| D | FRAGRANCE | qs |
|   | PRESERVATIVE | qs |
|   | SODIUM HYDROXIDE | qs pH = 7 approximately |

[1] Sodium ($C_{14}$—$C_{16}$)olefin sulfonate, marketed by the company AKZO

PROCEDURE:

Melt the APG in the water at about 60° C. Incorporate the oils (phase A). Allow to cool to 30° C. then incorporate phase B, followed by phase C and then phase D. Lastly, adjust the PH [sic].

CHARACTERISTICS:

Opaque emulsion-type appearance Viscosity 1000 mPa.s (Brookfield LVT4 6 rpm)

What is claimed is:

1. Concentrate for making a pearlescent composition or an emulsion, said concentrate comprising:

i) from 60 to 90% by weight of a mixture of at least one alkylglycoside selected from the group consisting of formula (I) and of at least one alkylglycoside selected from the group consisting of formula (II):

$$RO\,(G)_x \quad (I)$$
$$R'O\,(G')_{x'} \quad (II)$$

in which:

R represents a saturated or unsaturated linear or branched aliphatic radical containing from 8 to 15 carbon atoms, R' represents a saturated or unsaturated linear or branched aliphatic radical containing from 16 to 22 carbon atoms, G and G', which are identical or different, represent a saccharide residue, and x and x', which are identical or different, represent a number between 1 and 10; and ii) from 10 to 40% by weight of at least one fatty alcohol of formula $R_1OH$, $R_1$ representing a saturated or unsaturated linear or branched aliphatic radical containing from 8 to 22 carbon atoms.

2. Concentrate according to claim 1, wherein G and G' are identical and represent a glucose residue.

3. Concentrate according to claim 1, wherein x and x' represent a number between 1.05 and 2.5.

4. Concentrate according to claim 3, wherein x and x' represent a number between 1.05 and 1.35.

5. Concentrate according to claim 1, wherein the weight ratio between the at least one alkylglycoside of formula (I) and the at least one alkylglycoside of formula (II) is between 3/1 and 1/3.

6. Concentrate according to claim 5, wherein said weight ratio is between 2/1 and 1/2.

7. Concentrate according to claim 1, comprising a mixture of fatty alcohols, wherein the radical represented by $R_1$ of each of said fatty alcohols is identical to at least one of the radicals represented by R or R'.

8. Concentrate according to claim 7, wherein the fatty alcohol mixture comprises at least 80% by weight of said fatty alcohols in which the radical represented by $R_1$ contains 16 to 22 carbon atoms.

9. Concentrate according to claim 8, wherein the fatty alcohol mixture comprises from 90 to 99% by weight of said fatty alcohols.

10. Concentrate according to claim 1, comprising from 15 to 38% by weight of the at least one fatty alcohol.

11. Concentrate according to claim 10, comprising from 25 to 38% by weight of the at least one fatty alcohol.

12. Concentrate according to claim 1, wherein said $R^8$ contains 16 or 18 carbon atoms.

13. Concentrate according to claim 1, wherein R, R' and $R_1$ each represent a linear or branched alkyl radical.

14. A pearling base comprising a dispersion of the concentrate according to claim 1 in a liquid.

15. A pearling base according to claim 14, wherein the liquid is aqueous.

16. Cleansing soap comprising a concentrate according to claim 1 and at least one surfactant soap.

17. Cleansing soap according to claim 16, further comprising a softener.

18. Syndet comprising a concentrate according to claim 1, and at least one foaming surfactant.

19. Syndet according to claim 18, further comprising at least one composition selected from the group consisting of plasticizers, binders and texturizing agents.

20. Syndet according to claim 18, comprising 2 to 40% by weight of said concentrate, 20 to 50% by weight of said at least one foaming surfactant and 10 to 40% by weight of at least one composition selected from the group consisting of plasticizers, binders and texturizing agents.

21. Syndet according to claim 20, comprising 10 to 35% by weight of said concentrate.

22. A process for preparing a pearlescent composition or emulsion comprising:

selecting the concentrate according to claim 1, said concentrate acting as a pearling agent; and mixing the concentrate with a diluent to produce said pearlescent composition or said emulsion.

23. A process according to claim 22 wherein the pearlescent composition or said emulsion is a foaming composition, said foaming composition being selected from the group consisting of pharmaceutical, cosmetic and hygiene compositions.

24. A process according to claim 23, wherein said foaming composition is selected from the group consisting of shampoos, liquid soaps, shower gels, bubble baths, makeup-removing gels for the face, and washing-up detergents.

25. A process according to claim 23, wherein said foaming composition contains from 2–15% by weight of said concentrate.

26. A process for preparing an emulsion, said emulsion selected from the group consisting of water-in-oil, oil-in-water and oil-in-water-in-oil emulsions, comprising mixing the concentrate according to claim 1 with a diluent.

27. A process according to claim 26, wherein said emulsion comprises from 1 to 15% by weight of said concentrate.

28. A process according to claim 26, wherein said emulsion is a fluid emulsion.

29. A process according to claim 28, wherein said fluid emulsion is a milk.

30. Composition comprising at least one foaming surfactant, at least one emulsified oil phase and at least one concentrate according to claim 1.

31. Composition according to claim 30, consisting of a 2-in-1 shower gel.

* * * * *